(12) United States Patent
Friebe et al.

(10) Patent No.: US 7,097,854 B2
(45) Date of Patent: Aug. 29, 2006

(54) AMINO ALCOHOL DERIVATIVES, PROCESS FOR THEIR PRODUCTION AND PHARMACEUTICAL PREPARATIONS AND REAGENTS CONTAINING THESE COMPOUNDS

(75) Inventors: Walter-Gunar Friebe, Mannheim (DE); Nikolaos Dimoudis, Wielenbach (DE); Uwe Michaelis, Weilheim (DE); Bernhard Knipp, Kürten (DE)

(73) Assignee: MediGene Oncology GmbH, Munich (DE)

( * ) Notice: Subject to any disclaimer, the term of this patent is extended or adjusted under 35 U.S.C. 154(b) by 343 days.

(21) Appl. No.: 10/059,207

(22) Filed: Jan. 31, 2002

(65) Prior Publication Data

US 2003/0236266 A1    Dec. 25, 2003

Related U.S. Application Data

(63) Continuation of application No. 09/147,818, filed on May 12, 1999, now abandoned.

(30) Foreign Application Priority Data

Sep. 12, 1996  (DE) ............................... 196 37 043

(51) Int. Cl.
*A61K 9/127*   (2006.01)
*A61K 38/00*   (2006.01)
*A01N 43/04*   (2006.01)

(52) U.S. Cl. .............................. 424/450; 514/2; 514/44

(58) Field of Classification Search ................ 435/6; 544/401, 399; 514/849, 316, 326, 1, 44; 549/521, 560; 424/450
See application file for complete search history.

(56) References Cited

U.S. PATENT DOCUMENTS

| | | | |
|---|---|---|---|
| 3,689,494 A | 9/1972 | Simpson | |
| 5,491,263 A | 2/1996 | Rooney | |
| 5,635,487 A | 6/1997 | Wolff | |

FOREIGN PATENT DOCUMENTS

| | | |
|---|---|---|
| EP | 0 002 901 | 7/1979 |
| JP | 05 232 660 | 9/1993 |
| JP | 63 025 654 | 2/1998 |
| WO | 94 05624 | 3/1994 |
| WO | 95 25542 | 9/1995 |
| WO | 96 17823 | 6/1996 |
| WO | 97 00241 | 1/1997 |

OTHER PUBLICATIONS

Crooke, S., (Jul. 1998) Antisense Research and Applications, Chapter 1, Basic Principles of Antisense Therapeutics, Springer-Verlag Press, Berlin, Heidelberg, New York, p. 3.*
Orkin et al., (Dec. 1995) Report and recommendations of the panel to assess the NIH investment in research on gene therapy, pp. 1-23.*
Anderson, W.F., (Feb. 1998) Human gene therapy, Nature, 392:supp, pp. 25-30.*
Patent Abstracts of Japan, vol. 018, No. 163, Mar. 18, 1994 & JP 05 331118.*
Chemical Abstracts, vol. 78, No. 25, Jun. 25, 1973, and SV. Zikolova et all, Tr. Nauchnoizsled, Khim,-Farm. Inst., vol. 7, 1972, pp. 79-90.*
Verma et al (Nature 389: 239-242, 1997).*
Romano et al (Stem Cells 18: 19-39, 2000).*
Somia and Verma (Nature Reviews Genetics 1: 91-99, 2000).*
Patent Abstracts of Japan, vol. 95, No. 003, Apr. 28, 1995.
Patent Abstracts of Japan, vol. 018, No. 163, Mar. 18, 1994.
CAS Registry Handbook, 1965-1971, American Chemical Society XP002051753/ CN, reg. No. 5505-42-0.
CAS Registry Handbook, 1974 Suppl., American Chemical Society XP002051754/CN, reg. No. 45321-99-1.
Chemical Abstracts, vol. 71, No. 7, Aug. 18, 1996, abstr. No. 30380/XP002051755.
Chemical Abstracts, vol. 100, No. 1, Jan. 2, 1984, abstr. No. 6612f/XP002051756.
Chemical Abstracts, vol. 78, No. 25, Jun. 25, 1973, abstr. No. 159552p/XP002051757.
P. Hegyes, et al., "Synthesis and structural study of 1, 3-dioxa-6-aza-2-silacyclooctanes" Journal of Organometallic Chemistry, vol. 251, No. 3, 1983, pp. 289-294.
Sv. Zikolova et al., "Synthesis of N1-substituted N4-[bis(β-hydroxyethyl) amino]piperazines" TR. Nauchnoizsled. Khim-Farm. Inst., vol. 7, 1972, pp. 79-90.

* cited by examiner

*Primary Examiner*—Richard Schnizer
(74) *Attorney, Agent, or Firm*—Rothwell, Figg, Ernst & Manbeck, P.C.

(57) ABSTRACT

The present invention relates to new amino alcohol derivatives, process for the production thereof and medicaments and reagents containing these compounds.

33 Claims, No Drawings

AMINO ALCOHOL DERIVATIVES, PROCESS FOR THEIR PRODUCTION AND PHARMACEUTICAL PREPARATIONS AND REAGENTS CONTAINING THESE COMPOUNDS

This is a Continuation of application Ser. No. 09/147,818 filed May 12, 1999, now abandoned. The disclosure of the prior application is hereby incorporated by reference herein in its entity.

The present invention concerns new amino alcohol derivatives, a process for their production as well as pharmaceutical preparations and reagents which contain these substances.

The invention concerns pharmaceutical agents of the general formula I $$A-B-J_m-D-N\begin{matrix}(CH_2)_n-O-W-Y\\ (CH_2)_o-O-X-Z,\end{matrix} \quad (I)$$

in which

A denotes hydrogen, a group $NR_1R_2$, a group $NR_1(CH_2)_p NR_3R_4$, a group $(C=NH)NH_2$ or a pyridinyl residue, B and D are the same or different and each denotes a bond, a $C_1$ to $C_6$ alkylene residue or a group $NR_5$-$C_2$ to $C_6$ alkylene, J denotes piperidinediyl or piperazinediyl, W and X are the same or different and each denotes a bond or a carbonyl group, Y and Z are the same or different and each denotes a saturated or unsaturated hydrocarbon residue with 7 to 24 carbon atoms, $R_1$ to $R_5$ are the same or different and each represents hydrogen or a $C_1$ to $C_6$ alkyl residue, m is an integer 0, 1 or 2 and if m equals 2 both residues J can the same or different, n and o are the same or different and each denotes the integers 2, 3 or 4 and p denotes an integer from 2 to 6 as well as physiologically tolerated salts thereof, provided that hydrazine derivatives are not included and than m cannot be 0 if A denotes hydrogen or a group $(C=NH)NH_2$ and B and D being the same or different represent a bond or an alkylene residue.

The alkyl, alkylene and hydrocarbon residues encompassed by the meanings of B, D, Y, Z and $R_1$ to $R_5$ can be straight-chained or branched. A pyridinyl residue is understood as an unsubstituted pyridine or a pyridine optionally substituted several-fold with straight-chained or branched $C_1$–$C_6$.

Values of 1 or 2 are preferred for m. Compounds of the general formula I are just as preferred which contain more than 2 nitrogens or, if A denotes $(C=NH)NH_2$, those that contain more than 3 nitrogens.

The invention in addition concerns new amino alcohol derivatives of the general formula I $$A-B-J_m-D-N\begin{matrix}(CH_2)_n-O-W-Y\\ (CH_2)_o-O-X-Z,\end{matrix} \quad (I)$$

in which

A denotes hydrogen, a group $NR_1R_2$, a group $NR_1(CH_2)_p NR_3R_4$, a group $(C=NH)NH_2$ or a pyridinyl residue, B and D are the same or different and each denotes a bond, a $C_1$ to $C_6$ alkylene residue or a group $NR_5$-$C_2$ to $C_6$ alkylene, J denotes piperidinediyl or piperazinediyl, W and X are the same or different and each denotes a bond or a carbonyl group, Y and Z are the same or different and each denotes a saturated or unsaturated hydrocarbon residue with 7 to 24 carbon atoms, $R_1$ to $R_5$ are the same or different and each represents hydrogen or a $C_1$ to $C_6$ alkyl residue, m is an integer 0, 1 or 2 and if m equals 2 both residues J can the same or different, n and o are the same or different and each denotes the integers 2, 3 or 4 and p denotes an integer from 2 to 6 as well as physiologically tolerated salts thereof, provided that hydrazine derivatives are not included and than m cannot be 0 if A denotes hydrogen or a group $(C=NH)NH_2$ and B and D being the same or different represent a bond or an alkylene residue and that it does not include the compounds octadecanoic acid-[(3-diethylamino-propyl)imino]-bis(methyl-2,1-ethanediyl)-ester-hydrochloride octadecanoic acid-[(3-dimethylamino-propyl)imino]di-3,1-propanediyl ester-dihydrochloride octadecanoic acid-[(3-dimethylamino-propyl)imino]di-3,1-propanediyl ester octadecanoic acid-[(3-dimethylamino-propyl)imino]di-2,1-ethanediyl ester-hydrochloride docosanoic acid-2-[(3-dimethylamino-propyl)-[2-[(1-oxododecyl)oxy]ethyl]amino] ethyl ester hexadecanoic acid-[(2-(ethylmethylamino)ethyl]imino]di-2,1-ethanediyl ester octadecanoic acid-[(3-(dimethylamino)propyl]imino]di-2,1-ethanediyl ester octadecanoic acid-[(3-(dimethylamino)propyl]imino]di-2,1-ethanediyl ester-dihydrochloride hexadecanoic acid-[(2-(ethylmethylamino)ethyl]imino]di-2,1-ethanediyl ester N,N-Bis[3-(dodecyloxy)propyl]-1,2-ethanediamine octadecanoic acid-[[2-[(2-aminoethyl)amino]ethyl]imino]-di-2,1-ethanediyl ester stearic acid-iminobis-(ethyleneiminoethylene)-ester-monoacetate Within the sense of the present invention the following meanings in compounds of formula I are preferred independently of one another. This applies to compounds as well as to medicaments that contain such compounds and likewise also to the respective therapeutic applications of these compounds.

A denotes $NH_2$ or $N(CH_3)_2$ or

B and D are the same or different and denote a bond, a $C_1$–$C_3$ alkylene residue or if m=0 an $N(CH_3)C_3$ to $C_4$ alkylene residue or J denotes piperidinediyl or m denotes 0 or 1 or W and X each denote CO or Y denotes $C_{13}H_{27}$ or $C_{17}H_{33}$ or Z denotes $C_{13}H_{27}$ or $C_{17}H_{33}$ or n and o each denote 2.

Compounds are especially preferred which fulfill all the above-mentioned meanings simultaneously.

Compounds are especially preferred which fulfil all the above-mentioned meanings simultaneously.

The compounds of formula I have valuable pharmacological properties and in particular they can facilitate the transport of biologically active molecules into prokaryotic or eukaryotic cells. They are therefore particularly suitable for introducing proteins, nucleic acids such as e.g. DNA, cDNA, mRNA, PNA, antisense polynucleotides and therapeutically active low molecular compounds such as peptide hormones, cytostatic agents and antibiotics into target cells within or outside of the organism. The new compounds according to the invention are therefore particularly suitable for the efficient treatment of mammals by gene therapy preferably of human patients. These compounds are also suitable for the production of drug combinations in cancer therapy, antiviral therapy, infection therapy and in diseases caused by dysregulation. In contrast to viral carriers for gene constructs, non-viral gene ferries often have only a low immunogenicity. The efficiency and persistency of the gene expression mediated by non-viral gene ferries has, however, not yet been satisfactory. In addition to improving gene expression, the compounds of the general formula I have the advantage that they can be degraded relatively easily due to the $C_2$–$C_4$-alkyl-0 chains on the tertiary nitrogen N of formula I.

Apart from the compounds listed in the examples, the invention concerns in particular all substances which have all possible combinations of the meanings of the variables mentioned in the examples.

The process according to the invention for the production of compounds of formula I is characterized in that a compound of the general formula II

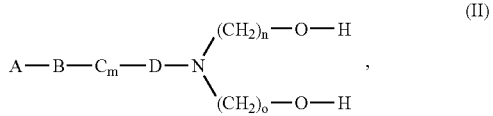

(II)

in which A, B, J, D, m, n and o have the above-mentioned meaning is reacted with a compound of the general formula III and a compound of the general formula IV

in which W, X, Y and Z have the above-mentioned meaning and E and G represent reactive residues, and subsequently if desired a protecting group contained in A, B or D is cleaved-off, a hydrogen atom representing A is converted into a group (C=NH)NH$_2$, a compound present as an acid addition salt is converted into the free base or a compound present as a base is converted by neutralization with a non-toxic acid into a physiologically tolerated salt.

The reactive residues E and G are nucleofuge groups such as for example halogen atoms, sulfonate or sulfate groups or acidic residues of activated esters, anhydrides or mixed anhydrides.

It is expedient to react compounds of formula II with compounds of formulae III and IV in an inert solvent such as an ether, for example tetrahydrofuran or an amide such as dimethylformamide or in pyridine optionally in the presence of a base such as triethylamine or ethyldiisopropylamine or an alkali alcoholate, however, the reagents of the general formulae III or IV can be used undiluted or, if W and X represent a carbonyl group, an acid such as acetic acid or trifluoroacetic acid can be used as the solvent.

Cleavage of a protecting group contained in A, B or D is carried out depending on the chemical characteristics of this group, for example by acidic or basic hydrolysis or hydrogenolysis. An acid cleavable protecting group is for example the tert.-butoxycarbonyl residue. A hydrogen atom representing A can for example be converted into an amidino group by reaction with cyanamide or pyrazol-1-carboxamidine.

The majority of the starting compounds of the general formula II are new (especially if m represents 1 or 2) and are also a subject matter of the invention. They can be produced from known starting materials by methods known in the literature.

Potential pharmacologically acceptable salts are in particular salts with non-toxic inorganic or organic acids such as for example hydrochloric acid, sulfuric acid, phosphoric acid, hydrobromic acid, acetic acid, trifluoroacetic acid, lactic acid, citric acid, malic acid, benzoic acid, salicylic acid, malonic acid, maleic acid, succinic acid or diaminocaproic acid.

The salts are obtained in the usual manner for example by neutralizing the compounds of formula I with the corresponding acids.

In order to produce pharmaceutical preparations or transfer reagents the compounds according to the invention are combined individually or as a combination, if desired using co-lipids, with a biologically active molecule, for example a polynucleotide, in a suitable ratio and administered in vivo or in vitro in a liquid preferably aqueous, or solid preferably lyophilized form. The in vivo administration can be carried out orally, parenterally, topically, transmucosally or by introduction into a body cavity of the patient. A delayed release from a biologically degradable matrix or administration as an aerosol or inhalable powder application is also possible.

The administered dose depends on the age, health and weight of the recipient, the extent of the disease, the type of other treatments which may be carried out at the same time, the frequency of the treatments and the type of the desired effect and can be determined experimentally by a person skilled in the art.

The following compounds are preferred within the sense of the invention in addition to the substances mentioned in the examples:

1. Oleic acid-2-[(2-oleoyloxy-ethyl)-piperidin-4-yl-methyl)-amino]-ethyl ester
2. Tetradecanoic acid-2-[(2-tetradecanoyloxy-ethyl)-piperidin-4-yl-methyl)-amino]-ethyl ester
3. Dodecanoic acid-2-[(2-dodecanoyloxy-ethyl)-piperidin-4-yl-methyl)-amino]-ethyl ester
4. Oleic acid-2-[(2-oleoyloxy-ethyl)-[1,4']bipiperidinyl-4-yl-amino]-ethyl ester
5. Tetradecanoic acid-2-{(2-tetradecanoyloxy-ethyl)-[3-[1,4']bipiperidinyl-4-ylamino)-propyl]-amino}-ethyl ester 6. Dodecanoic acid-2-{(2-dodecanoyloxy-ethyl)-[3-([1,4']bipiperidinyl-4-ylamino)-propyl]-amino}-ethyl ester
7. Oleic acid-2-{(2-oleoyloxy-ethyl)-[3-(3,4,5,6-tetrahydro-2H-[1,4']bipyridinyl-4-ylamino)-propyl]-amino}-ethyl ester
8. Dodecanoic acid-2-[{3-[3-dimethylamino-propyl)-methyl-amino]-propyl}-(2-dodecanoyloxy-ethyl)-amino]-ethyl ester
9. Tetradecanoic acid-2-[{3-[(3-dimethylamino-propyl)-methyl-amino]-propyl}-(2-tetradecanoyloxy-ethyl)-amino]-ethyl ester
10. Dodecanoic acid-2-[{3-[(3-diethylamino-propyl)-methyl-amino]-propyl}-(2-dodecanoyloxy-ethyl)-amino]-ethyl ester
11. Tetradecanoic acid-2-[{3-[(3-diethylamino-propyl)-methyl-amino]-propyl}-(2-tetradecanoyloxy-ethyl)-amino]-ethyl ester
12. Dodecanoic acid-2-{[3-(4-amino-butylamino)-propyl]-(2-dodecanoyloxy-ethyl)-amino}-ethyl ester
13. Dodecanoic acid-2-{(2-dodecanoyloxy-ethyl)-[1-(2-amino-ethyl)-piperidin-4-yl]-amino}-ethyl ester
14. Oleic acid-2-{(2-oleoyloxy-ethyl)-[1-(2-amino-ethyl)-piperidin-4-yl]-amino}-ethyl ester
15. Dodecanoic acid-2-{(2-dodecanoyloxy-ethyl)-[1-(2-amino-ethyl)-piperidin-4-yl-methyl]-amino}-ethyl ester
16. Oleic acid-2-{(2-oleoyloxy-ethyl)-[1-(2-amino-ethyl)-piperidin-4-yl-methyl]-amino}-ethyl ester
17. Dodecanoic acid-2-{[2-(4-amino-piperidin-1-yl)-ethyl]-(2-dodecanoyloxy-ethyl)-amino}-ethyl ester
18. Dodecanoic acid-2-{[4-(4-amino-piperidin-1-yl)-butyl]-(2-dodecanoyloxy-ethyl)-amino}-ethyl ester
19. Tetradecanoic acid-2-{[2-(4-amino-piperidin-1-yl)-ethyl]-(2-tetradecanoyloxy-ethyl)-amino}-ethyl ester
20. Tetradecanoic acid-2-{[4-(4-amino-piperidin-1-yl)-butyl]-(2-tetradecanoyloxy-ethyl)-amino}-ethyl ester
21. Oleic acid-2-{[2-(4-amino-piperidin-1-yl)-ethyl]-(2-oleoyloxy-ethyl)-amino}-ethyl ester
22. Oleic acid-2-{[4-(4-amino-piperidin-1-yl)-butyl]-(2-oleoyloxy-ethyl)-amino}-ethyl ester
23. Oleic acid-2-{(2-oleoyloxy-ethyl)-[1-(2-amino-ethyl)-piperidin-4-yl]-amino}-ethyl ester
24. Oleic acid-2-{(2-oleoyloxy-ethyl)-[1-(3-amino-propyl)-piperidin-4-yl-methyl]-amino}-ethyl ester
25. Oleic acid-2-{(2-oleoyloxy-ethyl)-[1-(2-amino-ethyl)-piperidin-4-yl-methyl]-amino}-ethyl ester
26. 4-Dimethylamino-1-{3-[bis-(2-tetradecyloxy-ethyl)-amino]-propyl}-piperidine
27. 4'-{[Bis-(2-tetradecanoyloxy-ethyl)]-amino}-[4,1']bipiperidine-1-carboxamidine

EXAMPLE 1

Decanoic acid-2-{(2-decanoyloxy-ethyl)-[3-(4-methyl-piperazin-1-yl)-propyl]-amino}-ethyl ester-hydrochloride 2.1 ml (15 mmol) triethylamine is added to a solution of 1.35 g (5.5 mmol) 2-{(2-hydroxy-ethyl)-[3-(4-methyl-piperazin-1-yl)-prpyl]-amino}-ethanol in 30 ml tetrahydrofuran, a solution of 2.3 ml (11 mmol) decanoyl chloride in 20 ml tetrahydrofuran is added dropwise and it is heated for 20 h to reflux. After cooling it is filtered, the filtrate is concentrated by evaporation and the residue is chromatographed on silica gel. 1.28 g of the desired compound is eluted as an oil with ethyl acetate/methanol 1:1, this is dissolved in ethyl acetate and admixed with excess ethereal hydrogen chloride solution. After concentrating the solution by evaporation the precipitate is removed by filtration and 1.3 g of the title compound (42% of theory) of melting point 208–212° C. is isolated.

The 2-{(2-hydroxy-ethyl)-[3-(4-methyl-piperazin-1-yl)-propyl]-amino}-ethanol used as the starting material can be obtained as follows:

50 mg potassium iodide is added to a solution of 4.1 g (40 mmol) diethanolamine and 7.8 g (44 mmol) 3-(4-methyl-piperazin-1-yl)-propyl chloride in 40 ml dimethyl-formamide and heated for 5 h to 60° C. After concentrating in a vacuum, the residue is chromatographed on silica gel. 2.7 g (27% of theory) of the desired compound is eluted as an oil using ethyl acetate/methanol 1:1.

EXAMPLE 2

Oleic acid-2-{(2-oleoyloxy-ethyl)-[3-(4-methyl-piperazin-1-yl)-propyl]-amino}-ethyl ester-hydrochloride The title compound is obtained as an oil in an analogous manner to that described in example 1 from 2-{(2-hydroxy-ethyl)-[3-(4-methyl-piperazin-1-yl)-propyl]-amino}-ethanol and oleoyl chloride in a yield of 35%.

EXAMPLE 3

Oleic acid-2-[(2-oleoyloxy-ethyl)-(3,4,5,6-tetrahydro-2H-[1,4']bipyridinyl-4-yl-amino]-ethyl ester-hydrochloride The title compound is obtained as a viscous oil in an analogous manner to that described in example 1 from 2-hydroxyethyl-(3,4,5,6-tetrahydro-2H-[1,4']bipyridinyl-4-yl)-amino]-ethanol and oleoyl chloride in a yield of 53%.

The 2-hydroxy-ethyl-(3,4,5,6-tetrahydro-2H-[1,4']bipyridinyl-4-yl)-amino]-ethanol used as the starting material can be obtained as follows:

a) A mixture of 62.9 g (0.33 mol) 1-benzyl-piperidin-4-one, 34.8 g diethanolamine and 300 ml toluene is heated for 2 h to reflux on a water separator. After 5 ml water has been separated, it is concentrated and the residue is distilled in a vacuum. 73.2 g 2-(8-benzyl-1-oxa-4,8-diaza-spiro[4.5]-dec-4-yl)-ethanol (80% of theory) of b.p.$_{0.08}$ 185–190° C. is isolated.

b) A solution of 87.6 g (0.32 mol) of the previously described compound in 900 ml methanol is hydrogenated over 2 g platinum dioxide and subsequently over 2 g 10 percent palladium carbon at 4 bar hydrogen pressure. After the calculated amount of hydrogen has been taken up, it is filtered and concentrated. 55.0 g (91% of theory) 2-[(2-hydroxy-ethyl)-(piperidin-4-yl)-amino]-ethanol remain as an oil.

c) A mixture of 24 g (127 mmol) of the previously described compound and 7.2 g (64 mmol) 4-chloro-pyridine is heated for 2 h to 150° C., subsequently taken up in 10 N sodium hydroxide solution and extracted with dichloro methane and methanol. After concentrating the extract and triturating with ethyl acetate, 14.3 g (91% of theory) 2-[2-hydroxy-ethyl-(3,4,5,6-tetrahydro-2H-[1,4']bipyridinyl-4-yl)-amino]-ethanol of m.p. 126–128° C. remain.

EXAMPLE 4

Tetradecanoic acid-2-[(2-tetradecanoyloxy-ethyl)-(3,4,5,6-tetrahydro-2H-[1,4']bipyridinyl-4-yl)-amino]-ethyl ester-hydrochloride The title compound is obtained in an analogous manner to that described in example 1 in a 51% yield as an amorphous powder of melting range 100–120° C. from 2-[(2-hydroxy-ethyl)-(3,4,5,6-tetrahydro-2H-[1,4']bipyridinyl-4-yl)-amino]-ethanol and tetradecanoyl chloride.

EXAMPLE 5

Dodecanoic acid-2-[(2-dodecanoyloxy-ethyl)-3,4,5,6-tetrahydro-2H-[1,4']bipyridinyl-4-yl)-amino]-ethyl ester-hydrochloride The title compound is obtained as an amorphous powder in an analogous manner to that described in example 1 from 2-[(2-hydroxy-ethyl)-(3,4,5,6-tetrahydro-2H-[1,4']bipyridinyl-4-yl)-amino]-ethanol and dodecanoyl chloride in a yield of 48%.

EXAMPLE 6

Oleic acid-2-[(2-oleoyloxy-ethyl)-(3,4,5,6-tetrahydro-2H-[1,4']bipyridinyl-4-yl-methyl)-amino]-ethyl ester-hydrochloride The title compound is obtained as an oil in an analogous manner to that described in example 1 from 2-[(2-hydroxy-ethyl)-(3,4,5,6-tetrahydro-2H-[1,4']bipyridinyl-4-yl-methyl)-amino]-ethanol and oleoyl chloride in a yield of 37%.

The 2-hydroxyethyl-(3,4,5,6-tetrahydro-2H-[1,4']bipyridinyl-4-yl)-amino]-ethanol used as the starting material can be obtained as follows:
a) A mixture of 23.8 g (0.1 mol) 1-benzoyl-4-chloromethyl-piperidine and 21.0 g (0.1 mol) diethanolamine is heated for 1 h to 150° C., subsequently 10 N sodium hydroxide solution is added and it is extracted with dichloromethane. After concentration by evaporation, 30.4 g (99% of theory) 2-[(2-hydroxy-ethyl)-(1-benzoyl-piperidin-4-yl-methyl)-amino]-ethanol remain as an oil.
b) 30.3 g of the previously described compound is heated with 200 ml 6 N hydrochloric acid for 5 h to reflux. After cooling it is washed with diethyl ether, the aqueous phase is concentrated, it is made alkaline with 10 N sodium hydroxide solution, extracted with dichloro-methane, dried and concentrated by evaporation. 16.0 g (79% of theory) 2-[(2-hydroxy-ethyl)-(piperidin-4-yl-methyl)-amino]-ethanol remain as an oil.
c) 2-[(2-Hydroxy-ethyl)-(3,4,5,6-tetrahydro-2H-[1,4']bipyridinyl-4-yl-methyl)-amino]-ethanol is obtained as an oil analogously to the process described under 3c) from the previous compound and 4 chloro-pyridine in a 44% yield.

EXAMPLE 7

Tetradecanoic acid-2-[(2-tetradecanoyloxy-ethyl)-(3,4,5,6-tetrahydro-2H-[1,4']bipyridinyl-4-yl-methyl)-amino]-ethyl ester-hydrochloride The title compound is obtained as an oil in an analogous manner to that described in example 1 from 2-[(2-hydroxy-ethyl)-(3,4,5,6-tetrahydro-2H-[1,4']bipyridinyl-4-yl-methyl)-amino]-ethanol and tetradecanoyl chloride in an 86% yield.

EXAMPLE 8

Dodecanoic acid-2-[(2-dodecanoyloxy-ethyl)-(3,4,5,6-tetrahydro-2H-[1,4']bipyridinyl-4-yl-methyl)-amino]-ethyl ester-hydrochloride The title compound is obtained as an oil in an analogous manner to that described in example 1 from 2-[(2-hydroxy-ethyl)-(3,4,5,6-tetrahydro-2H-[1,4']bipyridinyl-4-yl-methyl)-amino]-ethanol and dodecanoyl chloride in an 81% yield.

EXAMPLE 9

Oleic acid-2-[(2-oleoyloxy-ethyl)-(3-piperidin-1-yl-propyl)-amino]-ethyl ester

The title compound is obtained as an oil in an analogous manner to that described in example 1 from 2-[(2-hydroxy-ethyl)-(3-piperidin-1-yl-propyl)-amino]-ethanol (J. Organomet. Chem. 251, 289 (1983)) and oleoyl chloride in a 39% yield.

EXAMPLE 10

Dodecanoic acid-2-{[3-(4-amino-piperidin-1-yl)-propyl]-2-dodecanoyloxy-ethyl)-amino}-ethyl ester 1.0 g (5 mmol) dodecanoyl chloride is added dropwise to a solution of 0.7 g (2 mmol) 2-{[3-(4-amino-piperidin-1-yl)-propyl]-2-hydroxy-ethyl)-amino}-ethanol-hydrochloride in 10 ml trifluoroacetic acid and it is stirred for 18 h at room temperature. It is concentrated by evaporation, admixed with 10 ml cold 1 N sodium hydroxide solution, extracted with ethyl acetate, concentrated by evaporation and chromatographed on silica gel. 0.87 g (71% of theory) of the desired compound is eluted as an oil with ethyl acetate/methanol 4:1.

The 2-{[3-(4-amino-piperidin-1-yl)-propyl]-(2-hydroxy-ethyl)-amino}-ethanol-hydrochloride used as the starting material can be obtained as follows:
a) A mixture of 56.2 g (0.2 mol) 4-benzamido-1-(3-chloro-propyl)-piperidine, 19.8 g (0.19 mol) diethanolamine, 16.6 g (0.12 mol) potassium carbonate and 500 ml n-propanol are heated for 32 h to reflux. It is filtered, the filtrate is concentrated by evaporation and chromatographed on silica gel. 33.2 g (48% of theory) 2-{[3-(4-benzamido-piperidin-1-yl)-propyl]-(2-hydroxy-ethyl)-amino}-ethanol is eluted with ethyl acetate/methanol 9:1 as an amorphous solid substance.
b) 17.2 g (0.05 mol) of the previous compound is refluxed for 18 h with 190 ml 6 N hydrochloric acid. It is allowed to cool, washed with dichloromethane and the aqueous phase is concentrated by evaporation. 17.0 g (96% of theory) 2-{[3-(4-amino-piperidin-1-yl)-propyl]-(2-hydroxy-ethyl)-amino}-ethanol-hydrochloride remain as an oil.

EXAMPLE 11

Tetradecanoic acid-2-{[3-(4-amino-piperidin-1-yl)-propyl]-(2-tetradecanoyloxy-ethyl)-amino}-ethyl ester The title compound is obtained as an oil in a 64% yield in an analogous manner to that described in example 10 from 2-{[3-(4-amino-piperidin-1-yl)-propyl-(2-hydroxy-ethyl)-amino}-ethanol-hydrochloride and tetradecanoyl chloride.

EXAMPLE 12

Oleic acid-2-[(2-oleoyloxy-ethyl)-(2-piperidin-4-yl-ethyl)-amino]-ethyl ester-hydrochloride 3.1 ml (9.5 mmol) oleoyl chloride is added to a solution of 0.95 g (3.8 mmol) 2-[(2-hydroxy-ethyl)-(2-piperidin-4-yl-ethyl)-amino]-ethanol-hydrochloride in 20 ml dimethylformamide and heated for 4 h to 50° C. It is concentrated by evaporation and chromatographed on silica gel. 0.4 g (14% of theory) of the title compound is eluted as an oil with ethyl acetate/methanol 9:1.

The 2-[(2-hydroxy-ethyl)-(2-piperidin-4-yl-ethyl)-amino]-ethanol used as a starting material can be obtained as follows:

1.0 g activated ruthenium oxide is added to a solution of 57 g (0.27 mol) 2-[(2-hydroxy-ethyl)-(2-pyridin-4-yl-ethyl)-amino]-ethanol (Chem. Abstr. 1960, 13129) in 700 ml methanol and hydrogenated for 16 h at 100° C. and 150 bar hydrogen pressure. It is filtered, concentrated by evaporation and chromatographed on silica gel. 47.9 g (82% of theory) of the desired compound is eluted as an oil with methanol.

EXAMPLE 13

Tetradecanoic acid-2-[(2-tetradecanoyloxy-ethyl)-(2-piperidin-4-yl-ethyl)-amino]-ethyl ester The title compound is obtained as an oil in a 71% yield in an analogous manner to that described in example 10 from 2-[(2-hydroxy-ethyl)-(2-piperidin-4-yl-ethyl)-amino]-ethanol and tetradecanoyl chloride.

EXAMPLE 14

Dodecanoic acid-2-[(2-dodecanoyloxy-ethyl)-(2-piperidin-4-yl-ethyl)-amino]-ethyl ester The title compound is obtained as an oil in a 90% yield in an analogous manner to that described in example 10 from 2-[(2-hydroxy-ethyl)-(2-piperidin-4-yl-ethyl)-amino]-ethanol and dodecanoyl chloride.

EXAMPLE 15

Tetradecanoic acid-2-{(2-tetradecanoyloxy-ethyl)-[2-(3,4,5,6-tetrahydro-2H-[1,4']bipyridinyl-4-yl)-ethyl]-amino}-ethyl ester The title compound is obtained as an oil in a 95% yield in an analogous manner to that described in example 10 from 2-{(2-hydroxy-ethyl)-[2-(3,4,5,6-tetrahydro-2H-[1,4']bipyridinyl-4-yl)-ethyl]-amino}-ethanol and tetradecanoyl chloride.

EXAMPLE 16

Dodecanoic acid-2-{(2-dodecanoyloxy-ethyl)-[2-(3,4,5,6-tetrahydro-2H-[1,4']bipyridinyl-4-yl)-ethyl]-amino}-ethyl ester The title compound is obtained as an oil in a 65% yield in an analogous manner to that described in example 10 from 2-{(2-hydroxy-ethyl)-[2-(3,4,5,6-tetrahydro-2H-[1,4']bipyridinyl-4-yl)-ethyl]-amino}-ethanol and dodecanoyl chloride.

EXAMPLE 17

Tetradecanoic acid-2-[(2-tetradecanoyloxy-ethyl)-[1,4']bipiperidinyl-4-yl-amino]-ethyl ester The title compound is obtained as an oil in a 35% yield in an analogous manner to that described in example 10 from 2-[(2-hydroxy-ethyl)-[1,4']bipiperidinyl-4-yl-amino]-ethanol and tetradecanoyl chloride.

The 2-[(2-hydroxy-ethyl)-[1,4']bipiperidinyl-4-yl-amino]-ethanol used as a starting material can be obtained as follows:

24 g (90 mmol) of the 2-[2-hydroxy-ethyl-(3,4,5,6-tetrahydro-2H-[1,4']bipyridinyl-4-yl)-amino]-ethanol described under 3c) is hydrogenated on ruthenium oxide analogously to the process described in example 12.17 g (70% of theory) of the desired compound is isolated as an oil.

EXAMPLE 18

Dodecanoic acid-2-[(2-dodecanoyloxy-ethyl)-[1,4']bipiperidinyl-4-yl-amino]-ethyl ester The title compound is obtained as an oil in a 32% yield in an analogous manner to that described in example 10 from 2-[(2-hydroxy-ethyl)-[1,4']bipiperidinyl-4-yl-amino]-ethanol and dodecanoyl chloride.

EXAMPLE 19

Oleic acid-2-{(2-oleoyloxy-ethyl)-[2-(3,4,5,6-tetrahydro-2H-[1,4']bipyridinyl-4-yl)-ethyl]-amino}-ethyl ester-hydrochloride The title compound is obtained as an oil in a 57% yield in an analogous manner to that described in example 1 from 2-{(2-hydroxy-ethyl)-[2-(3,4,5,6-tetrahydro-2H-[1,4']bipyridinyl-4-yl)-ethyl]-amino}-ethanol and oleoyl chloride.

EXAMPLE 20

Oleic acid-2-[(2-oleoyloxy-ethyl)-(1'-methyl-[1,4']bipiperidinyl-4-yl)-amino]-ethyl ester The title compound is obtained as an oil in a 37% yield in an analogous manner to that described in example 1 from 2-[(2-hydroxy-ethyl)-(1'-methyl-[l,4']bipiperidinyl-4-yl)-amino]-ethanol and oleoyl chloride.

The 2-[(2-hydroxy-ethyl)-(1'-methyl-[1,4']bipiperidinyl-4-yl)-amino)-ethanol used as a starting material can be obtained as follows:

a) 5.4 g (20 mmol) of the 2-[(2-hydroxy-ethyl)-[1,4']bipiperidinyl-4-yl-amino]-ethanol described in example 17 is refluxed for 5 h with 20 ml ethyl formate and 1 ml water and subsequently concentrated by evaporation. 6.2 g (quantitative) 2-[(2-hydroxy-ethyl)-(1'-formyl-[1,4']bipiperidinyl-4-yl)-amino]-ethanol remain as an oil.

b) 6.0 g (20 mmol) of the previously described compound is added dropwise to a suspension of 2.9 g lithium tetrahydridoaluminate in 150 ml tetrahydrofuran and subsequently refluxed for 3 h. After standing overnight, ethyl acetate and saturated saline solution are added, it is filtered and the filtrate is concentrated by evaporation. It is chromatographed on silica gel and 1.8 g (32% of theory) 2-[(2-hydroxy-ethyl)-(1'-methyl-[1,4']bipiperidinyl-4-yl)-amino]-ethanol is eluted as an oil with ethyl acetate/methanolic ammonia 9:1.

EXAMPLE 21

Dodecanoic acid-2-{(2-dodecanoyloxy-ethyl)-[1-(3-amino-propyl)-piperidin-4-yl]-amino}-ethyl ester The title compound is obtained as an oil in a 37% yield in an analogous manner to that described in example 10 from 2-{(2-hydroxy-ethyl)-[1-(3-amino-propyl)-piperidin-4-yl]-amino}-ethanol and dodecanoyl chloride.

The 2-{(2-hydroxy-ethyl)-[1-(3-amino-propyl)-piperidin-4-yl]-amino}-ethanol used as a starting material can be obtained as follows:

a) A mixture of 5.5 g (29 mmol) of the 2-[(2-hydroxy-ethyl)-(piperidin-4-yl)-amino]-ethanol described in 3b), 60 ml methanol and 1.9 ml (29 mmol) acrylonitrile is stirred for 24 g at room temperature and subsequently concentrated in a vacuum. 6.7 g (96% of theory) 2-{(2-hydroxy-ethyl)-[1-(2-cyano-ethyl)-piperidin-4-yl]-amino}-ethanol remain as an oil.
b) 6.7 g (28 mmol) of the previously described compound is hydrogenated over Raney-nickel in 150 ml methanolic ammonia at 100° C. and 100 bar hydrogen pressure. It is filtered, concentrated by evaporation and 6.8 g (quantitative) 2-{(2-hydroxy-ethyl)-[1-(3-amino-propyl)-piperidin-4-yl]-amino}-ethanol is obtained as an oil.

EXAMPLE 22

Tetradecanoic acid-2-{(2-tetradecanoyloxy-ethyl)-[1-(3-amino-propyl)-piperidin-4-yl]-amino}-ethyl ester The title compound is obtained as an oil in a 34% yield in an analogous manner to that described in example 10 from 2-{(2-hydroxy-ethyl)-[1-(3-amino-propyl)-piperidin-4-yl]-amino}-ethanol and tetradecanoyl chloride.

EXAMPLE 23

Dodecanoic acid-2-{(2-dodecanoyloxy-ethyl)-[1-(3-amino-propyl)-piperidin-4-yl-methyl]-amino}-ethyl ester The title compound-is obtained as an oil in a 44% yield in an analogous manner to that described in example 10 from 2-{(2-hydroxy-ethyl)-[1-(3-amino-propyl)-piperidin-4-yl-methyl]-amino}-ethanol and dodecanoyl chloride.

The starting material used can be obtained from the compound of example 6b) by reaction with acrylonitrile analogously to example 21a) and subsequent hydrogenation analogously to example 21b).

EXAMPLE 24

Tetradecanoic acid-2-{(2-tetradecanoyloxy-ethyl)-[1-(3-amino-propyl)-piperidin-4-yl-methyl]-amino}-ethyl ester The title compound is obtained as an oil in a 38% yield in an analogous manner to that described in example 10 from 2-{(2-hydroxy-ethyl)-[1-(3-amino-propyl)-piperidin-4-yl-methyl]-amino}-ethanol and tetradecanoyl chloride.

EXAMPLE 25

Tetradecanoic acid-2-{(2-tetradecanoyloxy-ethyl)-[3-(3,4,5,6-tetrahydro-2H-[1,4']bipyridinyl-4-ylamino)-propyl]-amino}-ethyl ester The title compound is obtained as an oil in a 29% yield in an analogous manner to that described in example 10 from 2-{(2-hydroxy-ethyl)-[3-(3,4,5,6-tetrahydro-2H-[1,4'3bipyridinyl-4-ylamino)-propyl]-amino}-ethanol and tetradecanoyl chloride.

The 2-{(2-hydroxy-ethyl)-[3-(3,4,5,6-tetrahydro-2H-[1,4']bipyridinyl-4-ylamino)-propyl]-amino}-ethanol used as a starting material can be obtained as follows:

a) A solution of 46 g (0.4 mol) 4-chloropyridine and 123.5 g (0.86 mol) 4-piperidone ethylene ketal is refluxed for 48 h in 400 ml p-xylene. It is cooled, filtered, the filtrate is concentrated by evaporation and chromatographed on silica gel. 79.7 g (90% of theory) 8-pyridin-4-yl-1,4-dioxa-8-aza-spiro[4.5]decane with a melting point of 65° C. is eluted with ethyl acetate/ammoniacal methanol 9:1.
b) A solution of 79.7 g of the previously described ketal in 2 l tetrahydrofuran is admixed with 1000 ml 6 N hydrochloric acid and stirred for 2 h at room temperature. It is concentrated by evaporation, made basic with semi-concentrated ammonia water and extracted with dichloromethane. After concentrating the extract by evaporation 64.2 g (quantitative) 2,3,5,6-tetrahydro-[1,4']bipyridin-4-one of melting point 102° C. remains.
c) A mixture of 15 g (85 mmol) of the previously described ketone, 13.8 g (85 mmol) 2-[3-amino-propyl)-(2-hydroxy-ethyl)-amino]-ethanol (J. Am. Chem. Soc. 66, 728 (1944)), 100 mg 4-toluene sulfonic acid and 200 ml toluene is heated for 3 h on a water separator and subsequently concentrated by evaporation. The residue is taken up in 200 ml methanol, 500 mg platinum dioxide is added and it is hydrogenated for 10 h at 1 bar hydrogen pressure. After filtration and concentration by evaporation, it is chromatographed on silica gel and 22.4 g 2-{(2-hydroxy-ethyl)-[3-(3,4,5,6-tetrahydro-2H-[1,4']bipyridinyl-4-ylamino)-propyl]-amino}-ethanol is (fluted as an oil with ethyl acetate/methanol 1:1.

EXAMPLE 26

Dodecanoic acid-2-{(2-dodecanoyloxy-ethyl)-[3-(3,4,5,6-tetrahydro-2H-[1,4']bipyridinyl-4-ylamino)-propyl]-amino}-ethyl ester The title compound is obtained as an oil in a 34% yield in an analogous manner to that described in example 10 from 2-{(2-hydroxy-ethyl)-[3-(3,4,5,6-tetrahydro-2H-[1,4']bipyridinyl-4-ylamino)-propyl]-amino}-ethanol and dodecanoyl chloride.

EXAMPLE 27

Oleic acid-2-{(2-oleoyloxy-ethyl)-[1'-(3-dimethylamino-propyl)-[1,4']bipiperidinyl-4-yl]-amino}-ethyl ester The title compound is obtained as an oil in a 23% yield an analogous manner to that described in example 1 from 2-{(2-hydroxy-ethyl)-[1'-(3-dimethylamino-propyl)-[1,4']bipiperidinyl-4-yl]-amino}-ethanol and oleoyl chloride.

The 2-{(2-hydroxy-ethyl)-[1'-(3-dimethylamino-propyl)-[1,4']bipiperidinyl-4-yl]-amino}-ethanol used as the starting material can be obtained as follows:

A mixture of 4.05 g (15 mmol) of the 2-[(2-hydroxy-ethyl)-[1,4']bipiperidinyl-4-yl-amino]-ethanol described in example 17, 2.0 g potassium-carbonate, 2.2 g 3-dimethylamino-propyl chloride and 25 ml n-propanol is refluxed for 5 h, cooled, filtered and the filtrated is concentrated by evaporation. It is chromatographed on silica gel and 2.0 g (37% of theory) of the desired compound is eluted as an oil with ethyl acetate/methanolic ammonia 1:1.

EXAMPLE 28

Oleic acid-2-{[3-(4-dimethylamino-piperidin-1-yl)-propyl]-(2-oleoyloxy-ethyl)-amino}-ethyl ester The title compound is obtained as an oil in a 65% yield in an analogous manner to that described in example 1 from 2-{[3-(4-dimethylamino-piperidin-1-yl)-propyl)-(2-hydroxy-ethyl)-amino}-ethanol and oleoyl chloride.

The 2-{[3-(4-dimethylamino-piperidin-1-yl)-propyl]-(2-hydroxy-ethyl)-amino}-ethanol used as a starting material can be obtained as follows:
a) 4-Dimethylamino-piperidine is obtained as an oil in a 75% yield by hydrogenation over ruthenium oxide from 4-dimethylamino-pyridine analogously to the precursor described under example 12.
b) A mixture of 15.6 g (0.15 mol) diethanolamine, 30.9 g (0.3 mol) 1-bromo-3-chloro-propane, 300 ml tetrahydrofuran and 12.6 g potassium carbonate is refluxed for 5 h, filtered, concentrated by evaporation and chromatographed on silica gel. 16.7 g (62% of theory) N-(3-chloro-propyl)-diethanolamine is eluted as an oil with ethyl acetate/methanol 9:1.
c) A mixture of 1.92 (15 mmol) of the piperidine a), 2.72 g (15 mmol) of the halogenide b), 1.2 g potassium carbonate and 50 ml n-propanol is refluxed for 6 h, filtered, concentrated by evaporation and chromatographed on silica gel. 2.7 g (66% of theory) 2-{[3-(4-dimethylamino-piperidin-1-yl)-propyl]-(2-hydroxy-ethyl)-amino}-ethanol is eluted as an oil with ethyl acetate/methanolic ammonia 1:1.

EXAMPLE 29

Oleic acid-2-{(2-oleoyloxy-ethyl)-[1-(3-dimethylamino-propyl)-piperidin-4-yl]-amino}-ethyl ester The title compound is obtained as an oil in a 24% yield in an analogous manner to that described in example 1 from 2-{(2-hydroxy-ethyl)-[1-(3-dimethylamino-propyl)-piperidin-4-yl]-amino}-ethanol and oleoyl chloride.

The 2-{(2-hydroxy-ethyl)-[1-(3-dimethylamino-propyl)-piperidin-4-yl]-amino}-ethanol used as the starting material can be obtained as follows:

A mixture of 5.84 g (30 mmol) of the 2-[(2-hydroxy-ethyl)-(piperidin-4-yl)-amino]-ethanol described under 3b), 4.0 g (33 mmol) 3-dimethylamino-propyl chloride, 2.5 g potassium carbonate and 20 ml n-propanol is refluxed for 5 h, filtered, concentrated by evaporation and chromatographed on silica gel. 4.4 g (54% of theory) of the desired compound is eluted as an oil with ethyl acetate/methanolic ammonia 1:1.

EXAMPLE 30

Oleic acid-2-{[3-(4-amino-piperidin-1-yl)-propyl]-(2-oleoyloxy-ethyl)-amino}-ethyl ester A suspension of 4.5 g (4 mmol) of the 2-{[3-(4-amino-piperidin-1-yl)-propyl]-(2-hydroxy-ethyl)-amino}-ethanol-hydrochloride described in example 10 in 100 ml dichloromethane is admixed with 3.5 g N-ethyl-diisopropylamine and 0.87 g (4 mmol) pyrocarbonic acid di-t-butyl ester, it is refluxed for 18 h, a solution of 2.4 g (8 mmol) oleoyl chloride in 40 ml dichloromethane is added dropwise, it is refluxed for 18 h, admixed with 15 ml etheric hydrogen chloride solution and stirred for 6 h at room temperature. It is concentrated by evaporation, adjusted to pH 9 with N sodium hydroxide solution, extracted with dichloromethane and methanol, dried and concentrated by evaporation. After chromatography on silica gel (eluting agent ethyl acetate/methanol 1:1) 1.1 g (36% of theory) of the title compound is isolated as an oil.

EXAMPLE 31

Oleic acid-2-{[3-(4-aminomethyl-piperidin-1-yl)-propyl]-(2-oleoyloxy-ethyl)-amino}-ethyl ester The title compound is obtained as an oil in a 28% yield in an analogous manner to that described in example 30 from 2-{[3-(4-amino-methyl-piperidin-1-yl)-propyl]-(2-hydroxy-ethyl)-amino }-ethanol and oleoyl chloride.

The 2-{[3-(4-aminomethyl-piperidin-1-yl)-propyl]-(2-hydroxy-ethyl)-amino}-ethanol used as the starting material can be obtained from 4-aminomethyl-piperidine analogously to the compound described under 28c.

EXAMPLE 32

Oleic acid-2-[(2-oleoyloxy-ethyl)-(1'-ethyl-[1,4']bipiperidinyl-4-yl)-amino]-ethyl ester The title compound is obtained as an oil in a 22% yield in an analogous manner to that described in example 1 from 2-[(2-hydroxy-ethyl)-(1'-ethyl-[1,4']bipiperidinyl-4-yl)-amino]-ethanol and oleoyl chloride.

The 2-[(2-hydroxy-ethyl)-(1'-ethyl-[1,4']bipiperidinyl-4-yl)-amino]-ethanol used as the starting material can be obtained as follows:
a) 5.4 g (20 mmol) of the 2-[(2-hydroxy-ethyl)-[1,4']bipiperidinyl-4-yl-amino]-ethanol described in example 17 is stirred for 5 h at room temperature in 20 ml dimethylformamide and 60 ml dichloromethane containing 1.6 ml acetyl chloride and 1.7 g sodium hydrogen carbonate. It is filtered, dried and concentrated by evaporation. 6.4 g (quantitative) 2-[(2-hydroxy-ethyl)-(1'-acetyl-[1,4']bipiperidinyl-4-yl)-amino]-ethanol remains as an oil.
b) 5.6 g (18 mmol) of the previously described compound is reduced analogously to example 20b). 2.1 g (39% of theory) 2-[(2-hydroxy-ethyl)-(1'-ethyl-[1,4']bipiperidinyl-4-yl)-amino]-ethanol is obtained as an oil.

EXAMPLE 33

Oleic acid-2-{(2-oleoyloxy-ethyl)-[1-(3-amino-propyl)-piperidin-4-yl]-amino}-ethyl ester The title compound is obtained as an oil in a 25% yield in an analogous manner to that described in example 30 from 2-{(2-hydroxy-ethyl)-[1-(3-amino-propyl)-piperidin-4-yl]-amino}-ethanol (example 21b) and oleoyl chloride.

EXAMPLE 34

Tetradecanoic acid-2-{(2-tetradecanoyloxy-ethyl)-[1-(3-dimethylamino-propyl)-piperidin-4-yl-methyl]-amino}-ethyl ester The title compound is obtained as an oil in a 31% yield in an analogous manner to that described in example 10 from 2-{(2-hydroxy-ethyl)-[1-(3-dimethylamino-propyl)-piperidin-4-yl-methyl]-amino}-ethanol and tetradecanoyl chloride.

The 2-{(2-hydroxy-ethyl)-[1-(3-dimethylamino-propyl)-piperidin-4-yl-methyl]-amino}-ethanol used as the starting material can be obtained as follows:

2-{(2-Hydroxy-ethyl)-[1-(3-dimethylamino-propyl)-piperidin-4-yl-methyl]-amino}-ethanol is obtained as an oil in a 29% yield analogously to the process described in example 27 by alkylation of the compound described in example 6b) with 3-dimethylamino-propyl chloride.

EXAMPLE 35

Oleic acid-2-{(2-oleoyloxy-ethyl)-[1-(3-dimethylamino-propyl)-piperidin-4-yl-methyl]-amino}-ethyl ester The title compound is obtained as an oil in a 26% yield in an analogous manner to that described in example 1 from 2-{(2-hydroxy-ethyl)-[1-(3-dimethylamino-propyl)-piperidin-4-yl-methyl]-amino}-ethanol and oleoyl chloride.

EXAMPLE 36

Tetradecanoic acid-2-{(2-tetradecanoyloxy-ethyl)-2-[[1-(3-amino-propyl)-piperidin-4-yl]-ethyl]-amino}-ethyl ester The title compound is obtained as an oil in a 44% yield in an analogous manner to that described in example 10 from 2-{(2-hydroxy-ethyl)-2-[[1-[3-amino-propyl)-piperidin-4-yl]-ethyl]-amino}-ethanol and tetradecanoyl chloride.

The 2-{(2-hydroxy-ethyl)-2-[[1-(3-amino-propyl)-piperidin-4-yl]-ethyl]-amino}-ethanol used as the starting material can be obtained analogously to the reaction procedure described in examples 21a) and 21b) from acrylonitrile and the precursor of example 12 (yield 47%)

EXAMPLE 37

Dodecanoic acid-2-{(2-dodecanoyloxy-ethyl)-2-[[1-(3-amino-propyl)-piperidin-4-yl]-ethyl]-amino}-ethyl ester The title compound is obtained as an oil in a 61% yield in an analogous manner to that described in example 10 from 2-{(2-hydroxy-ethyl)-2-[[1-(3-amino-propyl)-piperidin-4-yl]-ethyl]-amino}-ethanol and dodecanoyl chloride.

EXAMPLE 38

Tetradecanoic acid-2-{(2-tetradecanoyloxy-ethyl)-2-[[1-(3-dimethylamino-propyl)-piperidin-4-yl]-ethyl]-amino}-ethyl ester The title compound is obtained as an oil in a 50% yield in an analogous manner to that described in example 1 from 2-{(2-hydroxy-ethyl)-2-[[1-(3-dimethylamino-propyl)-piperidin-4-yl]-ethyl]-amino}-ethanol and tetradecanoyl chloride.

The 2-{(2-hydroxy-ethyl)-2-[[1-(3-dimethylamino-propyl)-piperidin-4-yl]-ethyl]-amino}-ethanol used as the starting material can be obtained in a 66% yield from the precursor of example 12 and 3-dimethylamino-propyl chloride analogously to the precursor of example 27.

EXAMPLE 39

Oleic acid-2-{(2-oleoyloxy-ethyl)-2-[[1-(3-dimethyl-amino-propyl)-piperidin-4-yl]-ethyl]-amino}-ethyl ester The title compound is obtained as an oil in a 41% yield in an analogous manner to that described in example 1 from 2-{(2-hydroxy-ethyl)-2-[[1-(3-dimethylamino-propyl)-piperidin-4-yl]-ethyl]-amino}-ethanol and oleoyl chloride.

EXAMPLE 40

Tetradecanoic acid-2-{[3-(4-(2-amino-ethyl)-piperidin-1-yl)-propyl]-(2-tetradecanoyloxy-ethyl)-amino}-ethyl ester 32% of the theoretical yield of the title compound is obtained as an oil in an analogous manner to that described in example 10 from 2-{[3-(4-(2-amino-ethyl)-piperidin-1-yl)-propyl]-(2-hydroxy-ethyl)-amino}-ethanol and tetradecanoyl chloride.

The 2-{[3-(4-(2-amino-ethyl)-piperidin-1-yl]-propyl]-(2-hydroxy-ethyl)-amino}-ethanol used as the starting material can be obtained as follows:

a) Hydrogenation of 4-(2-amino-ethyl)-pyridine (J. Am. Chem. Soc. 78, 4129 (1956)) yields 4-(2-amino-ethyl)-piperidine in a yield of 68% in an analogous procedure to that described in example 12.

b) 9.0 g (70 mmol) of the previous compound is heated for 1 h to 150° C. with 6.4 g (35 mmol) of the compound from example 28b). It is allowed to cool, taken up in 15 ml 2 N sodium hydroxide solution and made strongly alkaline with 10 N sodium hydroxide solution. After extraction with dichloromethane, drying and concentrating the extract by evaporation it is chromatographed on silica gel. 6.0 g (63% of theory) 2-{[3-(4-(2-amino-ethyl)-piperidin-1-yl)-propyl]-(2-hydroxy-ethyl)-amino}-ethanol is eluted with ethyl acetate/methanol 3:1.

EXAMPLE 41

Dodecanoic acid-2-{[3-(4-(2-amino-ethyl)-piperidin-1-yl) -propyl]-(2-dodecanoyloxy-ethyl)-amino}-ethyl ester The title compound is obtained as an oil in 35% of the theoretical yield in an analogous manner to that described in example 10 from 2-{[3-(4-(2-amino-ethyl)-piperidin-1-yl)-propyl]-(2-hydroxy-ethyl)-amino}-ethanol and dodecanoyl chloride.

EXAMPLE 42

Dodecanoic acid-2-{[3-(4-(3-amino-propylamino)-piperidin-1-yl)-propyl]-(2-dodecanoyloxy-ethyl)-amino}-ethyl ester The title compound is obtained as an oil in 18% of the theoretical yield in an analogous manner to that described in example 10 from 2-{[3-(4-(3-amino-propylamino)-piperidin-1-yl)-propyl]-(2-hydroxy-ethyl)-amino}-ethanol and dodecanoyl chloride.

The 2-{[3-(4-(3-amino-propylamino)-piperidin-1-yl)-propyl]-(2-hydroxy-ethyl)-amino}-ethanol used as the starting material can be obtained as follows:

Reaction of the 2-{[3-(4-amino-piperidin-1-yl)-propyl]-(2-hydroxy-ethyl)-amino}-ethanol described in example 10 with acrylonitrile analogously-to example 21a) and subsequent hydrogenation analogously to example 21b) yields the desired compound as an oil.

EXAMPLE 43

Tetradecanoic acid-2-{[3-(4-(3-amino-propylamino)-piperidin-1-yl)-propyl]-(2-tetradecanoyloxy-ethyl)-amino}-ethyl ester The title compound is obtained as an oil in 12% of the theoretical yield in an analogous manner to that described in example 10 from 2-{[3-(4-(3-amino-propylamino)-piperidin-1-yl)-propyl]-(2-hydroxy-ethyl)-amino}-ethanol and tetradecanoyl chloride.

EXAMPLE 44

4-<2-{[Bis-(2-tetradecanoyloxy-ethyl)]-amino}-ethyl>-piperidine-1-carboxamidine

A mixture of 1.92 g (3 mmol) of the compound from example 13, 0.25 g cyanamide and 5 ml n-butanol is heated for 2 h to 120° C., cooled, the residue is taken up in dichloromethane, washed with a small amount of water, dried and concentrated by evaporation. After chromatography on silica gel 0.96 g (47% of theory) of the title compound is eluted as a wax with ethyl acetate/methanol 1:1.

EXAMPLE 45

N-[3-(4-<2[Bis-(2-tetradecanoyloxy-ethyl)-amino]-ethyl>-piperidin-1-yl)-propyl]-guanidine The title compound is obtained as an oil in a 64% yield in an analogous manner to that described in example 44 from the compound of example 36 and cyanamide.

EXAMPLE 46

Oleic acid-2-[(2-ethylamino-ethyl)-(2-oleoyloxy-ethyl)-amino]-ethyl ester-hydrochloride The title compound is obtained as an oil in a 36% yield in an analogous manner to that described in example 1 from 2-[(2-ethylamino-ethyl)-(2-hydroxy-ethyl)-amino]-ethanol and oleoyl chloride.

The 2-[(2-ethylamino-ethyl)-(2-hydroxy-ethyl)-amino]-ethanol used as the starting material can be obtained as follows:

11.0 g (58 mmol) N-{2-[bis-(2-hydroxy-ethyl)-amino]-ethyl}-acetamide (J. Med. Chem. 36, 1839 (1993)) is reduced analogously to example 20b). 8.3 g (81% of theory) of the desired compound is isolated as an oil.

EXAMPLE 47

Oleic acid-2-[(2-diethylamino-ethyl)-(2-oleoyloxy-ethyl)-amino]-ethyl ester-hydrochloride The title compound is obtained as an oil in a 44% yield in an analogous manner to that described in example 12 from 2-[(2-diethylamino-ethyl)-(2-hydroxy-ethyl)-amino]-ethanol and oleoyl chloride.

EXAMPLE 48

Oleic acid-2-[(2-amino-ethyl)-(2-oleoyloxy-ethyl)-amino]-ethyl ester-hydrochloride The title compound is obtained as an oil in a 25% yield in an analogous manner to that described in example 12 from 2-[(2-amino-ethyl)-(2-hydroxy-ethyl)-amino]-ethanol (J. Am. Chem. Soc. 81, 3984 (1959)) and oleoyl chloride.

EXAMPLE 49

Oleic acid-2-{[3-(3-amino-propylamino)-propyl]-(2-oleoyloxy-ethyl)-amino}-ethyl ester-hydrochloride The title compound is obtained as an oil in a 29% yield in an analogous manner to that described in example 12 from 2-{[3-(3-amino-propylamino)-propyl]-(2-hydroxy-ethyl)-amino}-ethanol and oleoyl chloride.

The 2-{[3-(3-amino-propylamino)-propyl]-(2-hydroxy-ethyl)-amino}-ethanol used as the starting material can be obtained by reaction of 2-[3-amino-propyl)-(2-hydroxy-ethyl)-amino]-ethanol (J. Am. Chem. Soc. 66, 728 (1944)) with acrylonitrile analogously to example 21a) and subsequentl hydrogenation analogously to example 21b). b.p.$_{0.06}$ 176–177° C.

EXAMPLE 50

Oleic acid-2-[(3-dimethylamino-propyl)-(2-oleoyloxy-ethyl)-amino]-ethyl ester-hydrochloride The title compound is obtained as an oil in a 65% yield in an analogous manner to that described in example 1 from 2-[(3-dimethylamino-propyl)-(2-hydroxy-ethyl)-amino]-ethanol and oleoyl chloride.

The 2-[(3-dimethylamino-propyl)-(2-hydroxy-ethyl)-amino]-ethanol used as the starting material can be obtained analogously to the procedure of example 27 from diethanolamine and 3-dimethylamino-propyl chloride. b.p.$_{1.5}$ 135–136° C.

EXAMPLE 51

Oleic acid-2-[(3-diethylamino-propyl)-(2-oleoyloxy-ethyl)-amino]-ethyl ester

The title compound is obtained as an oil in a 65% yield in an analogous manner to that described in example 1 from 2-[(3-diethylamino-propyl)-(2-hydroxy-ethyl)-amino]-ethanol (Chem. Pharm. Bull. 9, 313 (1961)) and oleoyl chloride.

EXAMPLE 52

Tetradecanoic acid-2-[(3-dimethylamino-propyl)-(2-tetradecanoyloxy-ethyl)-amino]-ethyl ester The title compound is obtained as an oil in a 78% yield in an analogous manner to that described in example 1 from 2-[(3-dimethyl-amino-propyl)-(2-hydroxy-ethyl)-amino]-ethanol and tetradecanoyl chloride.

EXAMPLE 53

Dodecanoic acid-2-[(3-dimethylamino-propyl)-(2-dodecanoyloxy-ethyl)-amino]-ethyl ester The title compound is obtained as an oil in a 79% yield in an analogous manner to that described in example 1 from 2-[(3-dimethylamino-propyl)-(2-hydroxy-ethyl)-amino]-ethanol and dodecanoyl chloride.

EXAMPLE 54

Tetradecanoic acid-2-[(3-diethylamino-propyl)-(2-tetradecanoyloxy-ethyl)-amino]-ethyl ester The title compound is obtained as an oil in a 50% yield in an analogous manner to that described in example 1 from 2-[(3-diethylamino-propyl)-(2-hydroxy-ethyl)-amino]-ethanol and tetradecanoyl chloride.

EXAMPLE 55

Dodecanoic acid-2-[(3-diethylamino-propyl)-(2-dodecanoyloxy-ethyl)-amino]-ethyl ester The title compound is obtained as an oil in a 60% yield in an analogous manner to that described in example 1 from 2-[(3-diethylamino-propyl)-(2-hydroxy-ethyl)-amino]-ethanol and dodecanoyl chloride.

EXAMPLE 56

Oleic acid-2-[{3-[(3-dimethylamino-propyl)-methyl-amino]-propyl}-(2-oleoyloxy-ethyl)-amino]-ethyl ester The title compound is obtained as an oil in a 63% yield in an analogous manner to that described in example 1 from 2-[{3-[(3-dimethylamino-propyl)-methyl-amino]-propyl}-(2-hydroxy-ethyl)-amino]-ethanol and oleoyl chloride.

The 2-[{3-[(3-dimethylamino-propyl)-methyl-amino]-propyl}-(2-hydroxy-ethyl)-amino]-ethanol used as the starting material can be obtained analogously to example 28c) by alkylation of N,N,N'-trimethyl-propane-1,3-diamine (J. Chem. Soc. (C) 1966, 527) with N-(3-chloro-propyl)-diethanolamine.

EXAMPLE 57

Oleic acid-2-[{3-[(3-diethylamino-propyl)-methyl-amino]-propyl}-(2-oleoyloxy-ethyl)-amino]-ethyl ester The title compound is obtained as an oil in a 59% yield in an analogous manner to that described in example 1 from 2-[{3-[(3-diethylamino-propyl)-methyl-amino]-propyl}-(2-hydroxy-ethyl)-amino]-ethanol and oleoyl chloride.

The 2-[{3-[(3-diethylamino-propyl)-methyl-amino]-propyl}-(2-hydroxy-ethyl)-amino]-ethanol used as the starting material can be obtained analogously to the precursor described in example-56 by alkylation of N,N-diethyl-N'-methyl-propane-1,3-diamine ("Monatsh. Chem. 112, 825 (1981)) with N-(3-chloro-propyl)-diethanolamine.

EXAMPLE 58

Dodecanoic acid-2-{[4-(3-amino-propylamino)-butyl]-(2-dodecanoyloxy-ethyl)-amino}-ethyl ester-hydrochloride The title compound is obtained as a wax in a 31% yield in an analogous manner to that described in example 10 from 2-{[4-(3-amino-propylamino)-butyl]-(2-hydroxy-ethyl)-amino}-ethanol and dodecanoyl chloride.

The 2-{[4-(3-amino-propylamino)-butyl]-(2-hydroxy-ethyl)-amino}-ethanol used as the starting material can be obtained 2-[(4-amino-butyl)-(2-hydroxy-ethyl)-amino]-ethanol (J. Am. Chem. Soc. 81, 3984 (1959)) and acrylonitrile analogously to example 21a) and subsequent hydrogenation analogously to example 21b).

EXAMPLE 59

Dodecanoic acid-2-{[3-(3-amino-propylamino)-propyl]-(2-dodecanoyloxy-ethyl)-amino}-ethyl ester-hydrochloride The title compound with a melting point of 245–246° C. is obtained in a 49% yield in an analogous manner to that described in example 10 from 2-{[3-(3-amino-propylamino)-propyl]-(2-hydroxy-ethyl)-amino}-ethanol (see example 49) and dodecanoyl chloride.

EXAMPLE 60

Tetradecanoic acid-2-{[4-(3-amino-propylamino)-butyl]-(2-tetradecanoyloxy-ethyl)-amino}-ethyl ester The title compound is obtained as an oil in a 27% yield in an analogous manner to that described in example 10 from 2-{[4-(3-amino-propylamino)-butyl]-(2-hydroxy-ethyl)-amino}-ethanol and tetradecanoyl chloride.

EXAMPLE 61

Tetradecanoic acid-2-[{3-[(3-dimethylamino-propyl)-methyl-amino]-propyl}-(2-tetradecanoyloxy-ethyl)-amino]-ethyl ester The title compound is obtained as an oil in a 35% yield in an analogous manner to that described in example 1 from 2-[{3-[(3-dimethylamino-propyl)-methyl-amino]-propyl}-(2-hydroxy-ethyl)-amino]-ethanol and tetradecanoyl chloride.

EXAMPLE 62

Tetradecanoic acid-2-[{3-[(3-diethylamino-propyl)-methyl-amino]-propyl}-(2-tetradecanoyloxy-ethyl)-amino]-ethyl ester The title compound is obtained as an oil in a 61% yield in an analogous manner to that described in example 1 from 2-[{3-[(3-diethylamino-propyl)-methyl-amino]-propyl}-(2-hydroxy-ethyl)-amino]-ethanol and tetradecanoyl chloride.

EXAMPLE 63

N-<3-{4-[Bis-(2-tetradecanoyloxy-ethyl)-amino]-piperidin-1-yl}-propyl>-guanidine The title compound is obtained as an oil in a 91% yield in an analogous manner to that described in example 44 from the compound of example 22 and cyanamide.

EXAMPLE 64

N-[3-(4-<[Bis-(2-tetradecanoyloxy-ethyl)-amino]-methyl>-piperidin-1-yl)-propyl]-guanidine The title compound is obtained as an oil in an 82% yield in an analogous manner to that described in example 44 from the compound of example 24 and cyanamide.

EXAMPLE 65

N-[2-(1-<3-[Bis-(2-tetradecanoyloxy-ethyl)-amino]-propyl>-piperidin-4-yl)-ethyl]-guanidine The title compound is obtained as an oil in a 94% yield in an analogous manner to that described in example 44 from the compound of example 40 and cyanamide.

EXAMPLE 66

Tetradecanoic acid-2-{(2-tetradecanoyloxy-ethyl)-[1-(2-amino-ethyl)-piperidin-4-yl]-amino}-ethyl ester The title compound is obtained as an oil in a 38% yield in an analogous manner to that described in example 10 from 2-{(2-hydroxy-ethyl)-[1-(2-amino-ethyl)-piperidin-4-yl]-amino}-ethanol and tetradecanoyl chloride.

The 2-{(2-hydroxy-ethyl)-[1-(2-amino-ethyl)-piperidin-4-yl]-amino}-ethanol used as the starting material can be obtained as follows:
a) A mixture of 8.5 g (45 mmol) of the 2-[(2-hydroxy-ethyl)-(piperidin-4-yl)-amino]-ethanol described in example 3b), 150 ml dimethylformamide, 3.4 g (45 mmol) chloroacetonitrile, 14.5. g potassium carbonate and 100 mg potassium iodide is stirred for 2 h at 60° C. It is filtered and the filtrate is concentrated by evaporation in a vacuum. 10.5 g (quantitative) 2-{(2-hydroxy-ethyl)-[1-cyanomethyl-piperidin-4-yl]-amino}-ethanol remains as an oily crude product.
b) 4.1 g (18 mmol) of the previously described compound is hydrogenated in 175 ml methanolic ammonia over Raney nickel at 35° C. and 100 bar hydrogen pressure. It is filtered, concentrated by evaporation and after chromatography on silica gel one obtains 2.3 g (55% of theory) 2{(2-hydroxy-ethyl)-1-(2-amino-ethyl)-piperidin-4-yl]-amino}-ethanol as an oil.

EXAMPLE 67

Tetradecanoic acid-2-{(2-tetradecanoyloxy-ethyl)-[1-(2-amino-ethyl)-piperidin-4-yl-methyl]-amino}-ethyl ester The title compound is obtained as an oil in a 29% yield in an analogous manner to that described in example 10 from 2-{(2-hydroxy-ethyl)-[1-(2-amino-ethyl)-piperidin-4-yl-methyl]-amino}-ethanol and tetradecanoyl chloride.

The 2-{(2-hydroxy-ethyl)-[1-(2-amino-ethyl)-piperidin-4-yl-methyl]-amino}-ethanol used as the starting material can be obtained as follows:
a) The intermediate product described in example 6b) is reacted with chloroacetonitrile analogously to the method described in example 66a).
b) The crude product obtained above is hydrogenated as in example 66b). The desired 2-{(2-hydroxy-ethyl)-[1-(2-amino-ethyl)-piperidin-4-yl-methyl]-amino}-ethanol is obtained in a yield of 47% of theory.

EXAMPLE 68

Tetradecanoic acid-2-{[3-(4-(aminomethyl)-piperidin-1-yl)-propyl]-(2-tetradecanoyloxy-ethyl)-amino}-ethyl ester The title compound is obtained as an oil in a 27% yield in an analogous manner to that described in example 10 from 2-{[3-(4-(aminomethyl)-piperidin-1-yl)-propyl]-(2-hydroxy-ethyl)-amino}-ethanol and tetradecanoyl chloride.

The 2-{[3-(4-aminomethyl-piperiain-1-yl)-propyl]-(2-hydroxy-ethyl)-amino}-ethanol used as the starting material can be obtained analogously to the compound described in example 28c from 4-aminomethyl-piperidine.

EXAMPLE 69

Tetradecanoic acid-2-{(2-tetradecanoyloxy-ethyl)-[1-(3-dimethylamino-propyl)-piperidin-4-yl]-amino}-ethyl ester The title compound is obtained as an oil in a 25% yield in an analogous manner to that described in example 10 from 2-{(2-hydroxy-ethyl)-[1-(3-dimethylamino-propyl)-piperidin-4-yl]-amino}-ethanol and tetradecanoyl chloride.

The 2-{(2-hydroxy-ethyl)-[1-(3-dimethylamino-propyl)-piperidin-4-yl]-amino}-ethanol used as the starting material is described in example 29.

EXAMPLE 70

Tetradecanoic acid-2-{[3-(4-dimethylamino-piperidin-1-yl)-propyl]-(2-tetradecanoyloxy-ethyl)-amino}-ethyl ester The title compound is obtained as an oil in a 62% yield in an analogous manner to that described in example 10 from 2-{[3-(4-dimethylamino-piperidin-1-yl)-propyl]-(2-hydroxy-ethyl)-amino}-ethanol and tetradecanoyl chloride.

The 2-{[3-(4-dimethylamino-piperidin-1-yl)-propyl]-(2-hydroxy-ethyl)-amino}-ethanol used as the starting material is described in example 28.

EXAMPLE 71

Tetradecanoic acid-2-{(2-tetradecanoyloxy-ethyl)-[1-(4-amino-butyl)-piperidin-4-yl]-amino}-ethyl ester The title compound is obtained as an oil in a 22% yield in an analogous manner to that described in example 10 from 2-{(2-hydroxy-ethyl)-[1-(4-amino-butyl)-piperidin-4-yl]-amino}-ethanol and tetradecanoyl chloride.

The 2-{(2-hydroxy-ethyl)-[1-(4-amino-butyl)-piperidin-4-yl]-amino}-ethanol used as the starting material can be obtained as follows:
a) A mixture of 18.8 g (100 mmol) of the 2-[(2-hydroxy-ethyl)-(piperidin-4-yl)-amino]-ethanol described in example 3b), 100 ml dimethyl-formamide, 11 ml (110 mmol) 4-bromo-butyronitrile, 18.9 ml N-ethyldiisopropylamine and 100 mg 4-dimethyl-amino-pyridine is stirred for 8 h at 90° C. and subsequently concentrated by evaporation in a vacuum. It is taken up in dichloromethane, filtered and the filtrate is concentrated. 15.0 g (59% of theory) 2-{(2-hydroxy-ethyl)-[1-(3-cyano-propyl)-piperidin-4-yl]-amino}-ethanol remains as an oil.
b) 15.0 g (59 mmol) of the previously described compound is hydrogenated in 300 ml methanolic ammonia over Raney nickel at 35° C. and 100 bar hydrogen pressure. It is filtered, concentrated by evaporation and 10.9 g (71% of theory) 2-{(2-hydroxy-ethyl)-[1-(4-amino-butyl)-piperidin-4-yl]-amino}-ethanol is obtained as an oil.

EXAMPLE 72

Tetradecanoic acid-2-{(2-tetradecanoyloxy-ethyl)-[1-(4-dimethylamino-butyl)-piperidin-4-yl]-amino}-ethyl ester The title compound is obtained as an oil in a 23% yield in an analogous manner to that described in example 10 from 2-{(2-hydroxy-ethyl)-[1-(4-dimethylamino-butyl)-piperidin-4-yl]-amino}-ethanol and tetradecanoyl chloride.

The 2-{(2-hydroxy-ethyl)-[1-(4-dimethylamino-butyl)-piperidin-4-yl]-amino}-ethanol used as the starting material can be obtained as follows:

4.7 ml formic acid and 5.6 ml saturated Formalin solution are added dropwise at 0° C. to 6.5 g (25 mmol) 2-{(2-hydroxy-ethyl)-[1-(4-amino-butyl)-piperidin-4-yl]-amino}-ethanol (example 71b) it is heated to 95–100° C. and stirred for a further 9 h. It is allowed to cool, admixed with 6.5 ml concentrated hydrochloric acid, refluxed for 3 h, made strongly alkaline with 10 N sodium hydroxide solution and extracted with dichloromethane. After drying and concentrating the extract by evaporation, 6.0 g (84% of theory) of the desired compound remain as an oil.

EXAMPLE 73

Tetradecanoic acid-2-{(2-tetradecanoyloxy-ethyl)-[1-(4-amino-butyl)-piperidin-4-yl-methyl]-amino}-ethyl ester The title compound is obtained as an oil in a 33% yield in an analogous manner to that described in example 10 from 2-{(2-hydroxy-ethyl)-[1-(4-amino-butyl)-piperidin-4-yl-methyl]-amino}-ethanol and tetradecanoyl chloride.

The 2-{(2-hydroxy-ethyl)-[1-(4-amino-butyl)-piperidin-4-yl-methyl]-amino}-ethanol used as the starting material can be obtained as follows:

The desired compound is obtained as an oil by reacting 2-[(2-hydroxy-ethyl)-(piperidin-4-yl-methyl)-amino]-ethanol (example 6b) with 4-bromo-butyronitrile analogously to example 71b) and subsequently hydrogenating analogously to example 71b).

EXAMPLE 74

Tetradecanoic acid-2-{(2-tetradecanoyloxy-ethyl)-[1-(4-dimethylamino-butyl)-piperidin-4-yl-methyl]-amino}-ethyl ester The title compound is obtained as an oil in a 43% yield in an analogous manner to that described in example 10 from 2-{(2-hydroxy-ethyl)-[1-(4-dimethylamino-butyl)-piperidin-4-yl-methyl]-amino}-ethanol and tetradecanoyl chloride.

The 2-{(2-hydroxy-ethyl)-[1-(4-dimethylamino-butyl)-piperidin-4-yl-methyl]-amino}-ethanol used as the starting material can be obtained (yield 69% of theory) from the 2-{(2-hydroxy-ethyl)-1-(4-amino-butyl)-piperidin-4-yl-methyl]-amino}-ethanol described under example 73 by the method described in example 72 by reaction with formic acid and Formalin solution.

EXAMPLE 75

Tetradecanoic acid-2-{(2-tetradecanoyloxy-ethyl)-2-[[1-(4-amino-butyl)-piperidin-4-yl]-ethyl]-amino}-ethyl ester The title compound is obtained as an oil in a 17% yield in an analogous manner to that described in example 10 from 2-{(2-hydroxy-ethyl)-2-[[1-(4-amino-butyl)-piperidin-4-yl]-ethyl]-amino}-ethanol and tetradecanoyl chloride.

The 2-{(2-hydroxy-ethyl)-2-[[1-(4-amino-butyl)-piperidin-4-yl]-ethyl]-amino}-ethanol used as the starting material can be obtained as follows:

The desired compound is obtained as an oil by reacting the 2-[(2-hydroxy-ethyl)-(2-piperidin-4-yl-ethyl)-amino]-ethanol described in example 12 with 4-bromo-butyronitrile analogously to example 71a) and subsequently hydrogenating analogously to example 71b).

EXAMPLE 76

Tetradecanoic acid-2-{(2-tetradecanoyloxy-ethyl)-2-[[1-(4-dimethylamino-butyl)-piperidin-4-yl]-ethyl]-amino}-ethyl ester The title compound is obtained as an oil in a 33% yield in an analogous manner to that described in example 10 from 2-{(2-hydroxy-ethyl) -2-[[1-(4-dimethylamino-butyl)-piperidin-4-yl]-ethyl]-amino}-ethanol and tetradecanoyl chloride.

The 2-{(2-hydroxy-ethyl)-2-[[1-(4-dimethylamino-butyl)-piperidin-4-yl]-ethyl]-amino}-ethanol used as the starting material can be obtained (yield 72% of theory) from the 2-{(2-hydroxy-ethyl)-2-[[1-(4-amino-butyl)-piperidin-4-yl]-ethyl]-amino}-ethanol described in example 75 by reaction with formic acid and Formalin solution according to the method described in example 72.

EXAMPLE 77

Pharmacological Testing

1. Test Principle

The testing of DOTAP or the compounds of the invention comprises transfection of the test cells, protein determination by means of the BCA method (Pierce) and carrying out a CAT Elisa and these are described here using DOTAP (Boehringer Mannheim) as an example. After ultrasonication the cationic lipid DOTAP forms unilamellar vesicles (liposomes) in aqueous solution which spontaneously form stable complexes with the DNA (pCMV-CAT). These complexes adhere to the cell surface, fuse with the cell membrane and pCMV-CAT is released into the cytoplasm. The transiently expressed CAT is detected in the cell lysate.

1.1 Test Cells

HeLa, human cancer epithelial cell line from the cervix, ATCC CCL 2

RPMI 1640, human cancer epithelial cell line from the nasal septum, ATCC CCL 30

CALU 1, human cancer epithelial cell line from the lung, ECACC 93120818 or another suitable test cell line 1.2 Test Medium The composition of the test medium used for the respective cell line corresponds with that of the respective culture medium, only the content of FCS is reduced by 50% (only 5% FCS instead of 10%).

2. Determination Procedure 2.1 Feeding Cells for the Test
  2.0 ml cell suspension ($1.5 \times 10^5$ cells/ml) are placed into each well of a 6-well multiplate
  incubate for 24 h at 37° C., 5% $CO_2$ 2.2 Transfection Mixture The DOTAP/DNA complexes are mixed in a sterile 96-well round-bottom plate.

EXAMPLE

60 µl HBS (Hank's buffered saline) buffer is added first, then 20 µl DOTAP is added. The DNA is diluted 1:20 with HBS. Then 40 µl=2 µg DNA is added to the transfection mixtures and mixed thoroughly. The mixture is allowed to stand for 15 min at room temperature.

Procedure for Transfection:
  aspirate TM (transfection medium) from all wells
  add 2 ml TM/well
  rapidly add the transfection mixtures
  thoroughly mix the content of the wells by gentle swirling
  incubate the cells for 6 h at 37° C., 5% $CO_2$
  afterwards aspirate the DOTAP/DNA mixture
  add 2 ml TM/well
  incubate the cells for 40–44 h, 37° C., 5% $CO_2$ 2.3 Lysing the Cells
  aspirate the TM and wash the cells twice with 2 ml ice-cold PBS/well, aspirate completely
  add 0.5 ml lysis buffer (from the CAT-Elisa kit, Boehringer Mannheim Co.) to the washed cells and allow to stand for 30 min at room temperature
  after 30 min transfer the lysates into Eppendorf cups and centrifuge for 10 min at 13000 rpm using a Biofuge
  remove an aliquot from the supernatant for the protein assay according to the BCA method. The remainder is shock-frozen with liquid nitrogen and stored at −80° C. until the CAT-Elisa is carried out.

2.4 Protein Determination of the Lysates Using the BCA (Bicinchoninic Acid) Method
  the BSA (bovine serum albumin) solution contained in the kit (Boehringer Mannheim Co.) is used to prepare protein standards by dilution with lysis buffer
  10 µl of the protein standard solution, the blank (lysis buffer) and the unknown sample are pipetted into a microtitre plate. 200 µl working solution is added to each well and the plate is shaken for 30 min on a shaker. After incubating for 30 min at 37° C. they are measured at 550 nm in an ELISA reader. The determination of the protein concentration is carried out using an evaluation program.

2.5 CAT-Elisa

Principle:

The CAT (chloroamphenicol acetyl transferase)-Elisa serves to quantitatively determine the CAT expression in eukaryotic cells after transfection with a plasmid that contains CAT as the reporter gene. The CAT-Elisa is a sandwich enzyme immunoassay. Anti-CAT antibodies are bound adsorptively to the walls of the modules. In the first step CAT from cell extracts specifically binds to the coated modules. In the second step the fixed CAT is bound by an ANTI-CAT antibody which is labelled with digoxigenin (anti-CAT-DIG). Anti-CAT-DIG is detected in the third step by a peroxidase-labelled antibody against digoxigenin (Anti-DIG-POD) and visualized in a subsequent substrate reaction.

Procedure:

The working steps of the CAT-Elisa are carried out according to the working instructions contained in the kit.

The microtitre plate is measured at 405 nm and a reference wavelength of 492 nm with an Elisa reader.

The pharmacological data are shown as an example in the following table:

| relative transfection efficiency in a CAT-Assay (DOTAP = 1) | | |
|---|---|---|
| compound of example | HeLa cells | Calu cells |
| 34 | 3.2 | 3.9 |
| 60 | 3.2 | 3.4 |

What is claimed is:

1. A composition comprising a compound of formula (I)

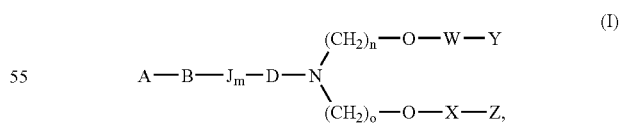

wherein

A is selected from the group consisting of hydrogen, a group $NR_1R_2$, a group $NR_1(CH_2)_pNR_3R_4$, a group $(C=NH)NH_2$ and a pyridinyl residue;

B and D are each independently selected from the group consisting of a bond, a $C_1$–$C_6$ alkylene residue and a group $NR_5$—($C_2$ to $C_6$ alkylene);

J is selected from the group consisting of piperidinediyl and piperazinediyl;

W and X are each independently selected from the group consisting of a bond and a carbonyl group;

Y and Z are each independently a saturated or unsaturated $C_7$–$C_{24}$ hydrocarbon residue;

$R_1$–$R_5$ are each independently selected from the group consisting of hydrogen and a $C_1$–$C_6$ alkyl residue;

m is 0, 1 or 2, wherein when m is 2, the two residues J are identical to or different from each other;

n and o are each independently 2, 3 or 4; and p is 2–6, or a physiologically tolerated salt thereof, and that m is other than 0 when A is either hydrogen or a group (C=NH)NH$_2$ and B and D are each independently a bond or an alkylene residue, wherein the composition further comprises a therapeutic agent.

2. The composition of claim 1, wherein m is 1 or 2.

3. The composition of claim 1, wherein the compound contains more than two nitrogens, or if A is (C=NH)NH$_2$, the compound contains more than three nitrogens.

4. The composition of claim 1, further comprising a nucleic acid.

5. A compound of formula (I), $$A-B-J_m-D-N\begin{matrix}(CH_2)_n-O-W-Y\\ (CH_2)_o-O-X-Z,\end{matrix}\quad (I)$$

wherein

A is selected from the group consisting of a group $NR_1R_2$, a group $NR_1(CH_2)_pNR_3R_4$, a group (C=NH)NH$_2$ and a pyridinyl residue;

B and D are each independently selected from the group consisting of a bond, a $C_1$–$C_6$ alkylene residue, and a group $NR_5$—($C_2$ to $C_6$ alkylene);

J is selected from the group consisting of piperidinediyl and piperazinediyl;

W and X are each independently selected from the group consisting of a bond and a carbonyl group;

Y and Z are each independently a saturated or unsaturated $C_7$–$C_{24}$ hydrocarbon residue;

$R_1$–$R_5$ are each independently selected from the group consisting of hydrogen and a $C_1$–$C_6$ alkyl residue;

m is 1 or 2, wherein when m is 2, the two residues J are identical to or different from each other;

n and o are each independently 2, 3 or 4; and p is 2–6, or a physiologically tolerated salt thereof.

6. The compound of claim 5, wherein A is NH$_2$ or N(CH3)$_2$.

7. The compound of claim 5, wherein B and D are each independently selected from the group consisting of a bond and a $C_1$–$C_3$ alkylene residue.

8. The compound of claim 5, wherein J is piperidinediyl.

9. The compound of claim 5, wherein m is 1.

10. The compound of claim 5, wherein W and X each are a carbonyl group.

11. The compound of claim 5, wherein Y is $C_{13}H_{27}$ or $C_{17}H_{33}$.

12. The compound of claim 5, wherein Z is $C_{13}H_{27}$ or $C_{17}H_{33}$.

13. The compound of claim 5, wherein n and o are each 2.

14. The compound of claim 5, wherein

A is NH$_2$ or N(CH$_3$)$_2$;

B and D are each independently selected from the group consisting of a bond and a $C_1$–$C_3$ alkylene residue;

J is piperidinediyl;

m is 1;

W and X each are a carbonyl group;

Y and Z are each independently $C_{13}C_{17}H_{27}$ or $H_{33}$; and n and o are each 2.

15. A composition comprising a compound as claimed in claim 5 and a therapeutic agent.

16. The composition of claim 15, further comprising a nucleic acid.

17. A compound of formula (II), $$A-B-J_m-D-N\begin{matrix}(CH_2)_n-O-H\\ (CH_2)_o-O-H,\end{matrix}\quad (II)$$

wherein

A is selected from the group consisting of a group $NR_1R_2$, a group $NR_1(CH_2)_pNR_3R_4$, a group (C=NH)NH$_2$ and a pyridinyl residue;

B is selected from the group consisting of a bond, a $C_1$–$C_6$ alkylene residue and a group $NR_5$—($C_2$ to $C_6$ alkylene);

D is selected from the group consisting of a $C_1$–$C_6$ alkylene residue and a group $NR_5$—($C_2$ to $C_6$ alkylene);

J is selected from the group consisting of piperidinediyl and piperazinediyl;

$R_1$–$R_5$ are each independently selected from the group consisting of hydrogen and a $C_1$–$C_6$ alkyl residue;

m is 1 or 2, wherein when m is 2, the two residues J are identical to or different from each other.

n and o are each independently 2, 3 or 4; and p is 2–6, or a physiologically tolerated salt thereof.

18. The compound of claim 17, wherein A is NH$_2$ or N(CH$_3$)$_2$.

19. The compound of claim 17, wherein B and D are each independently selected from the group consisting of a bond and a $C_1$–$C_3$ alkylene residue.

20. The compound of claim 17, wherein J is piperidinediyl.

21. The compound of claim 17, wherein m is 1.

22. The compound of claim 17, wherein n and o are each 2.

23. The compound of claim 17, wherein

A is NH$_2$ or N(CH$_3$)$_2$;

B and D are each independently selected from the group consisting of a bond and a $C_1$–$C_3$ alkylene residue;

J is piperidenediyl;

m is 1; and n and o are each 2.

24. A method of introducing a biologically active agent into a target cell, comprising combining the biologically active agent with a composition as claimed in claim 1 to produce a biologically active agent composition; and thereafter introducing the biologically active agent composition into the target cell.

25. The method of claim 24, wherein the target cell is a mammalian cell.

26. The method of claim 24, wherein the target cell is a human cell.

27. The method of claim 24, wherein the biologically active agent composition is introduced into the target cell in vitro.

28. The method of claim 24, wherein the biologically active agent is selected from the group consisting of a protein, a nucleic acid, a polynucleotide, a peptide hormone, a cytostatic agent and an antibiotic.

29. A method of introducing a biologically active agent into a target cell, comprising combining the biologically active agent with a compound as claimed in claim 5 to produce a biologically active agent composition; and thereafter introducing the biologically active agent composition into the target cell.

30. The method of claim 29, wherein the target cell is a mammalian cell.

31. The method of claim 29, wherein the target cell is a human cell.

32. The method of claim 29, wherein the biologically active agent composition is introduced into the target cell in vitro.

33. The method of claim 29, wherein the biologically active agent is selected from the group consisting of a protein, a nucleic acid, a polynucleotide, a peptide hormone, a cytostatic agent and an antibiotic.

* * * * *